United States Patent
Voss (10) Patent No.: US 11,445,165 B1
(45) Date of Patent: Sep. 13, 2022

(54) METHOD, SYSTEM AND COMPUTER READABLE STORAGE MEDIA FOR VISUALIZING A MAGNIFIED DENTAL TREATMENT SITE

(71) Applicant: DENTSPLY SIRONA INC., York, PA (US)

(72) Inventor: Bjoern Voss, Bensheim (DE)

(73) Assignee: DENTSPLY SIRONA INC., York, PA (US)

( * ) Notice: Subject to any disclaimer, the term of this patent is extended or adjusted under 35 U.S.C. 154(b) by 0 days.

(21) Appl. No.: 17/179,556

(22) Filed: Feb. 19, 2021

(51) Int. Cl.
| | |
|---|---|
| *H04N 13/268* | (2018.01) |
| *H04N 13/239* | (2018.01) |
| *H04N 13/257* | (2018.01) |
| *G06T 7/00* | (2017.01) |
| *H04N 13/194* | (2018.01) |
| *H04N 13/133* | (2018.01) |
| *A61B 90/00* | (2016.01) |

(52) U.S. Cl.
CPC ......... *H04N 13/268* (2018.05); *A61B 90/361* (2016.02); *G06T 7/0012* (2013.01); *H04N 13/133* (2018.05); *H04N 13/194* (2018.05); *H04N 13/239* (2018.05); *H04N 13/257* (2018.05); *A61B 2090/365* (2016.02); *G06T 2207/30036* (2013.01)

(58) Field of Classification Search
USPC .......................................................... 348/46
See application file for complete search history.

(56) References Cited

U.S. PATENT DOCUMENTS

| | | | |
|---|---|---|---|
| 8,120,847 B2 | 2/2012 | Chang | |
| 2002/0082498 A1 | 6/2002 | Wendt | |
| 2007/0098237 A1 | 5/2007 | Yoo | |
| 2011/0007137 A1* | 1/2011 | Rohaly | A61C 13/0004 348/50 |
| 2011/0102549 A1* | 5/2011 | Takahashi | G06T 19/00 348/46 |
| 2013/0076863 A1* | 3/2013 | Rappel | G02B 21/22 348/46 |
| 2013/0295518 A1 | 11/2013 | Parker | |
| 2015/0293345 A1 | 10/2015 | Laxhuber | |
| 2016/0191887 A1 | 6/2016 | Casas | |
| 2017/0007351 A1 | 1/2017 | Yu | |
| 2017/0202633 A1 | 7/2017 | Liu | |
| 2017/0215997 A1* | 8/2017 | Martin | A61B 1/05 |
| 2017/0352292 A1 | 12/2017 | Eid | |
| 2018/0168781 A1* | 6/2018 | Kopelman | G09B 23/283 |
| 2018/0192964 A1 | 7/2018 | Stalder | |

(Continued)

FOREIGN PATENT DOCUMENTS

| | | |
|---|---|---|
| BR | 102013030105 A2 | 3/2015 |
| CA | 2950028 A1 | 12/2015 |
| CA | 2991659 A1 | 1/2017 |

(Continued)

*Primary Examiner* — Behrooz M Senfi
(74) *Attorney, Agent, or Firm* — Dentsply Sirona Inc.

(57) ABSTRACT

A method, system and computer readable storage media for visualizing to a patient a magnified dental treatment site. By obtaining raw data from a stereo camera recording a dental treatment site, an enlarged, well-lit and spatially displayed view of the dental treatment site may be visualized in real time in augmented reality and virtual reality systems for diagnoses and treatment planning.

16 Claims, 5 Drawing Sheets

(56) References Cited

U.S. PATENT DOCUMENTS

2021/0192759 A1* 6/2021 Lang .................. A61C 5/40
2021/0361387 A1* 11/2021 Salah .................. A61C 7/002

FOREIGN PATENT DOCUMENTS

| | | |
|---|---|---|
| CN | 204427992 U | 7/2015 |
| CN | 104834091 A | 8/2015 |
| RU | 124555 U1 | 2/2013 |
| WO | 201102209 A2 | 1/2011 |
| WO | 2016106614 A1 | 7/2016 |
| WO | 2016108276 A1 | 7/2016 |

* cited by examiner

METHOD, SYSTEM AND COMPUTER READABLE STORAGE MEDIA FOR VISUALIZING A MAGNIFIED DENTAL TREATMENT SITE

FIELD OF THE INVENTION

The present application relates generally to a method, a system and computer readable storage media for visualizing a magnified dental treatment site and, more particularly, to a method, system and computer readable storage media for visualizing a data stream of stereo image pairs of a dental treatment site using an augmented reality or virtual reality device during dental treatment.

BACKGROUND OF THE INVENTION

Dentists use dental binocular loupes to provide a magnified visualization of an intraoral cavity for diagnosis of dental defects as well as for treatment planning.

The loupes are worn to enlarge a dentist's view of the mouth. This improves vision because objects in the field of view become bigger. Moreover the loupes allow dentists to have a more physiologic posture while working, and thereby minimizing slouching which dentists are historically known to develop.

However, the dentist may not be able to easily show the images to the patient or change the viewing angle in order to enable an optimal perspective for inspection of the treatment site.

U.S. Pat. No. 8,120,847B2 discloses a through-the-lens loupe with an interpupillary distance adjustment capability, the loupe including a pair of lenses, each lens having a telemicroscopic ocular cemented therethrough, and an upper portion, one on each side of a wearer's nose.

U.S. Patent Application Publication No. 20,150,293, 345A1 discloses magnification loupes which are equipped with one or more cameras and with one or more displays and/or with an audio assembly wherein the magnification loupes are configured to magnify a site without using magnifying optical systems.

US Patent Application No. 2,017,202,633 discloses an imaging and display system for guiding medical interventions comprising a wearable display for viewing by a user wherein the display presents a composite, or combined image that includes pre-operative surgical navigation images, intraoperative images, and in-vivo microscopy images or sensing data. A probe, such as a microscopy probe or a sensing probe, may be used to acquire in-vivo imaging/sensing data from the patient and the intra-operative and in-vivo images may be acquired using tracking and registration techniques to align them with the pre-operative image and the patient to form a composite image for display.

US Patent Application No. 20,020,082,498 discloses a method for image-guided surgery comprising capturing 3-dimensional (3D) volume data of a portion of a patient, processing the volume data so as to provide a graphical representation of the data, capturing a stereoscopic video view of a scene including a portion of said patient, rendering the graphical representation and the stereoscopic video view in a blended manner so as to provide a stereoscopic augmented image, and displaying said stereoscopic augmented image in a video-see-through display.

US Patent Application Publication No. 20,160,191,887 describes a real-time surgery navigation method and apparatus for displaying an augmented view of a patient from a static or dynamic viewpoint of a surgeon. A surface image, a graphical representation of the internal anatomic structure of the patient processed from preoperative or intraoperative images, and a computer geometrically registering both images may be used. Responsive to geometrically registering the images, a head mounted display may present to a surgeon an augmented view of the patient.

SUMMARY OF THE INVENTION

Existing limitations associated with the foregoing, as well as other limitations, can be overcome by a method, system and computer readable storage media for the visualization of a magnified dental treatment site.

In an aspect herein, the present invention may provide a method for visualizing a magnified dental treatment site, the method comprising: obtaining a data stream of stereo images from an intra-oral camera, the data stream of stereo images being a data stream of stereo image pairs that are offset and show the dental treatment site from slightly different perspectives; magnifying said data stream of stereo images; projecting a right and a left portion of the magnified data stream of stereo images in a field of view of a user of a first display device to create a combined view of the dental treatment site having a perception of 3D depth.

In another aspect herein, the method may further comprise one or more of the steps: (i) wherein the magnified data stream of stereo images is projected at a fixed distance and orientation relative to the field of view of the user, (ii) wherein visualization information is projected at variable distances and orientations relative to the field of view of the user, (iii) wherein the visualization information includes at least one of a magnification level, a resolution and a working distance, (iv) wherein the data stream of stereo images is magnified according to a predetermined magnification level, (v) further comprising changing a color space or contrast of the data stream of stereo images for diagnostic purposes, (vi) wherein said data stream of stereo images is obtained in real-time, (vii) further comprising overlaying the visualization information as an augmentation on a predetermined site in the field of view such that said visualization information appears directly superimposed on said predetermined site, (viii) further comprising projecting said magnified data stream of stereo images as virtual objects using a second display device adapted for virtual reality, (ix) further comprising displaying a magnified data stream from one stereo channel of the intra-oral camera on a monitor, (x) further comprising; updating the augmentation based on data selected from the group consisting of (i) real time output data from the intra-oral camera (ii) real time data tracking clinician movements and (iii) real time data tracking patient movements.

In another aspect, a system may be provided for visualizing a magnified dental treatment site, the system comprising: at least one processor configured to perform the steps of; obtaining a data stream of stereo images from an intra-oral camera, the data stream of stereo images being a data stream of stereo image pairs that are offset and show the dental treatment site from different orientations; magnifying said data stream of stereo images; projecting a right and a left portion of the magnified data stream of stereo images in a field of view of a user of a first display device to create a combined view of the dental treatment site having a perception of 3D depth.

The system may further comprise one or more of the configurations: (i) wherein the magnified data stream of stereo images is projected at a fixed distance and orientation relative to the field of view of the user, (ii) wherein visualization information is projected at variable distances and orientations relative to the field of view of the user, (iii) wherein the data stream of stereo images is magnified according to a predetermined magnification level, (iv) further comprising changing a color space or contrast of the data stream of stereo images for diagnostic purposes, (v) wherein said data stream of stereo images is obtained in real-time.

In another aspect, a non-transitory computer-readable storage medium may be provided. The non-transitory computer readable storage medium may store a program which, when executed by a computer system, causes the computer system to perform a procedure comprising: obtaining a data stream of stereo images from an intra-oral camera, the data stream of stereo images being a data stream of stereo image pairs that are offset and show the dental treatment site from different orientations; magnifying said data stream of stereo images; projecting a right and a left portion of the magnified data stream of stereo images in a field of view of a user of a first display device to create a combined view of the dental treatment site having a perception of 3D depth.

BRIEF DESCRIPTION OF THE DRAWINGS

Example embodiments will become more fully understood from the detailed description given herein below and the accompanying drawings, wherein like elements are represented by like reference characters, which are given by way of illustration only and thus are not limitative of the example embodiments herein and wherein.

Different ones of the figures may have at least some reference numerals that may be the same in order to identify the same components, although a detailed description of each such component may not be provided below with respect to each Figure.

DETAILED DESCRIPTION OF THE INVENTION

In accordance with example aspects described herein, a method, system and computer readable storage media may be provided for visualizing a magnified dental treatment site. By obtaining raw data from a stereo camera recording a dental treatment site, an enlarged, well-lit and spatially displayed view of the dental treatment site may be visualized in real time in augmented reality and virtual reality systems for diagnoses and treatment planning.

System for Visualizing A Magnified Dental Treatment Site

Figure 1:
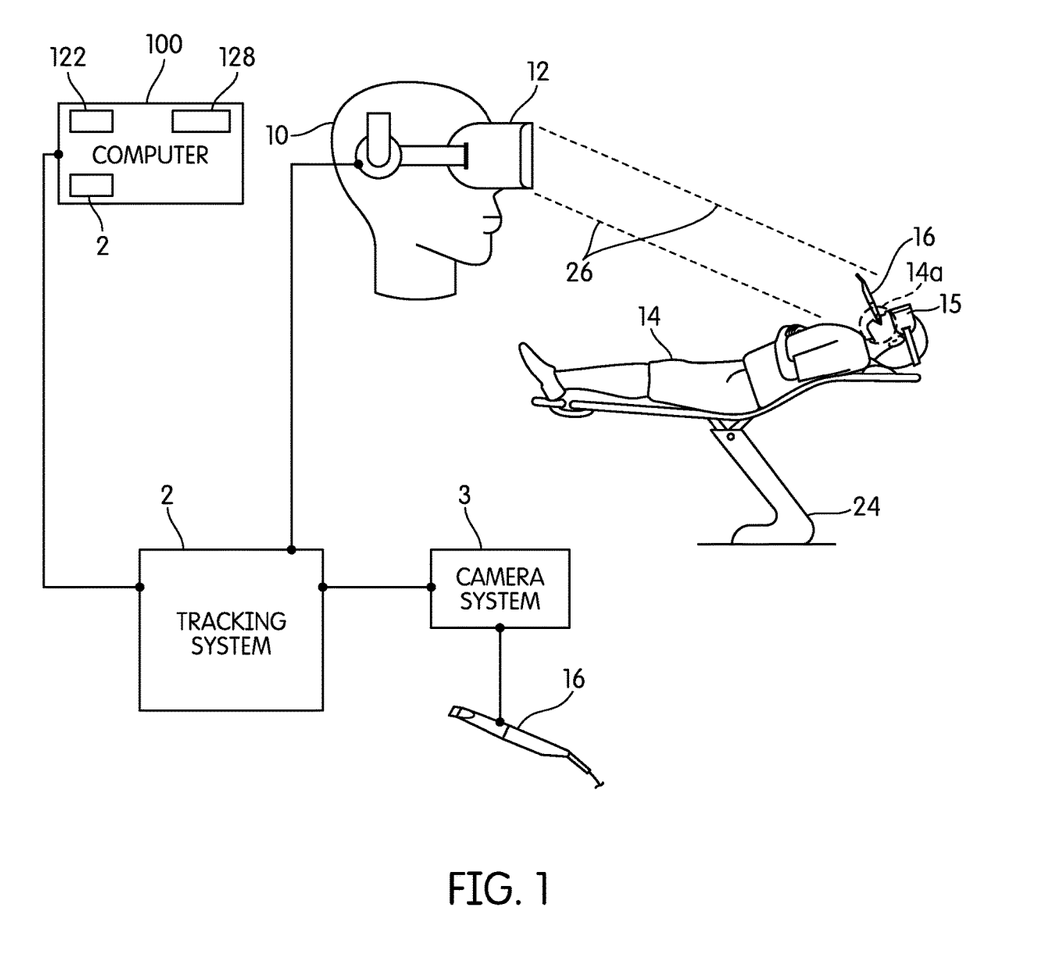
FIG. 1 is a block diagram illustrating a visualization system according to an embodiment of the present invention.
Figure 2A:
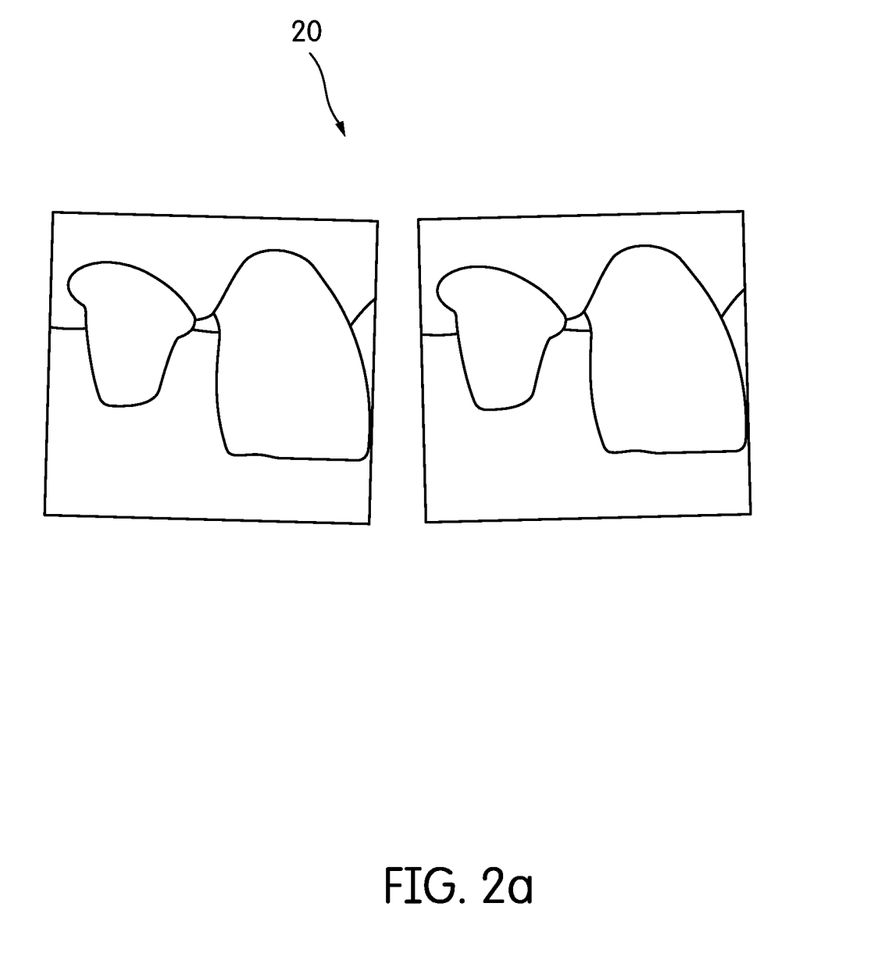
FIG. 2a is a sketch illustrating a stereo image pair according to an embodiment of the present invention.
Figure 2B:
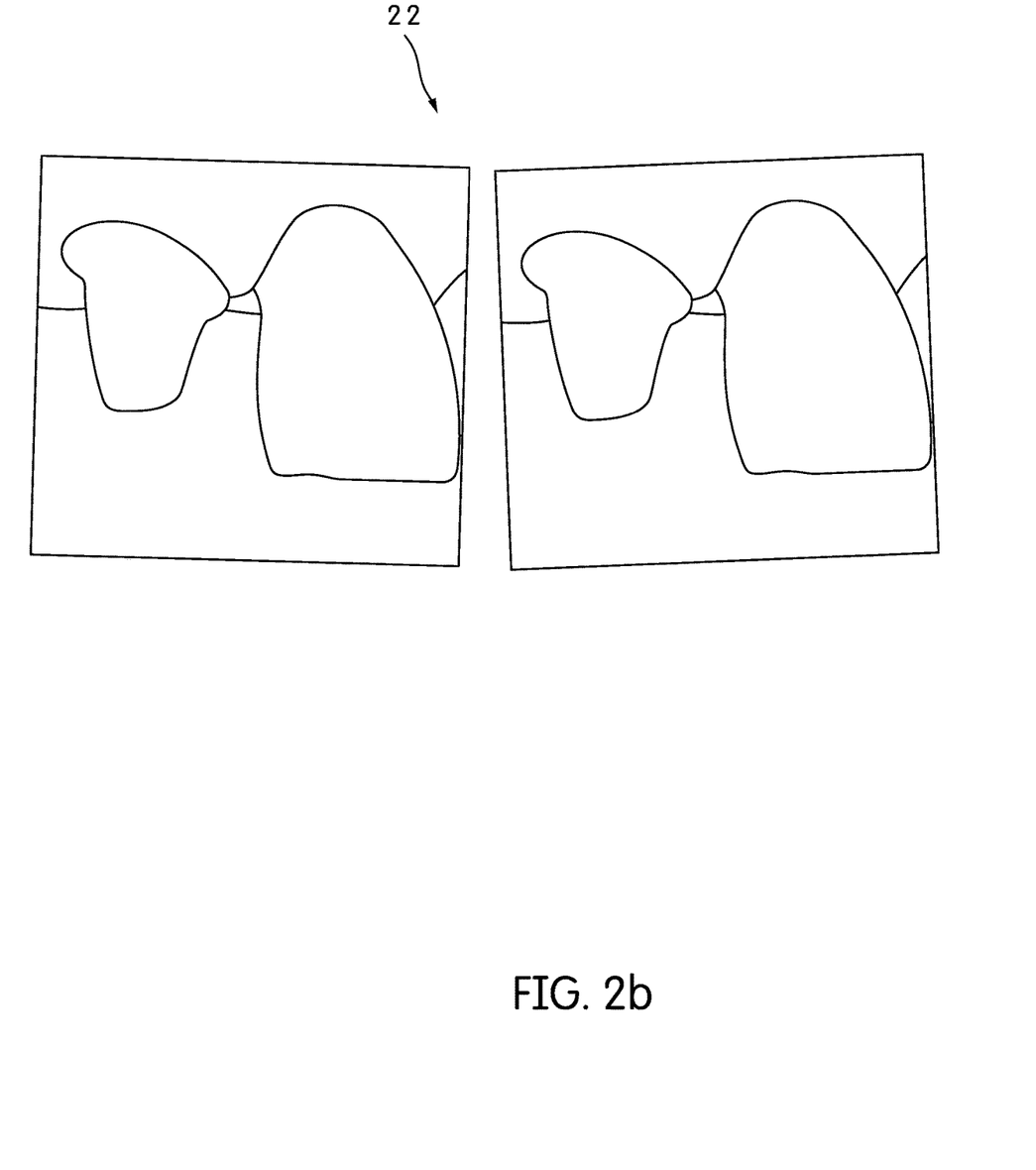
FIG. 2b is a sketch illustrating a magnified stereo image pair according to an embodiment of the present invention.

FIG. 1 illustrates a visualization system 1 comprising a first display device 12 for augmented visualization such as head mounted augmented reality glasses, an HUD display (head-up-display), or a stereoscopic display capable of receiving stereoscopic video images, or otherwise first display device 12 that may be adapted for receiving a data stream of stereo images 20 of a dental treatment site 14a for dental treatment. The data stream of stereo images 20 may preferably be a data stream of stereo image pairs that are magnified and displayed to the right and left eyes of a user such as a clinician 10 to give a perception of depth of the treatment site 14a. The magnified data stream of stereo images 22 may form three-dimensional videos and/or images. The data stream of stereo images 20 may be obtained in real time from an intra-oral camera 16 such as a dental stereo camera and may be magnified according to a predetermined magnification level or according to a magnification level determined by the clinician 10 such that the clinician 10 may see a magnified data stream of stereo images 22 in his/her field of view in real time. The magnification may be achieved through optical magnification camera optics or through digital magnification. Moreover the magnified data stream of stereo images 22 may be displayed on a second display device 15 such as a virtual reality device or 2D or 3D screen to show the magnified view of the treatment site 14a seen by the clinician 10 to the patient 14. In an illustrative embodiment, a stereo image pair is generated from an a 3D scene (e.g. from a 3D scanner). For this purpose, two synthetic stereo images would be calculated from the 3D scene, whereby the position of the virtual observer on the 3D scene differs by a certain stereo base for the two stereo images.

In an exemplary embodiment, each pair of the magnified stream of stereo images 22 are projected in a field of view of the clinician 10 by use of the first display device 12 in a first manner wherein a dimensionality of the projection is in a fixed XYZ plane. Herein the position and orientation of the magnified data stream of stereo images 22 relative to the field of view may be fixed. Each eye of the clinician 10 is in a different location, and as a result, each eye sees a slightly different image. The difference between these images allows the clinician 10 to perceive depth.

In another embodiment, information such as a magnification level, resolution, working distance, patient dental history and identification information or otherwise other visualization information may be additionally projected in a field of view of the clinician 10, said other visualization information being different from the magnified stream of stereo images 22. For example, an indication of the detection of caries through analysis of the data stream of stereo images 20, or an indication of the magnification level can be projected in a field of view of the of the clinician 10. Said other visualization information may be presented in a fixed orientation and distance from the eyes. Said other visualization information may be static and as such may require shifting focus from the patient to view.

In another exemplary embodiment, in order to limit shifting of the eyes to view said other visualization information, an augmented reality approach may be used wherein movements of the patient and clinician 10 are tracked in order to determine variable depth in the field of view at which said other visualization information can be projected for seamless viewing. This allows a more intuitive process for providing the clinician 10 with information to ensure seamless viewing without excessive shifting of the clinician 10 focus from the patient to the projected images. Tracking of the patient and clinician 10 are therefore used to determine an appropriate or variable position and depth in the field of view in which to project images. For example, the patient can be tracked to determine an empty space in the field of view in which said other visualization information can be projected without blocking a view of the patient.

In another embodiment, the first display device 12 may be designed to optionally project the magnified stream of stereo images 22 at variable positions and depths in the field of view of the clinician 10 instead of at a fixed position and depth. For example, the eyes (pupils) of the clinician 10 can be tracked to determine where in the field of view to display the magnified stream of stereo images 22 in order to create a seamless viewing of the patient and the stream.

Further magnified data stream of stereo images 22 (stereoscopic video) may be optionally overlaid in an augmented manner on a target site such as the intra oral cavity of the patient 14 or an environment of the clinician 10 within a field of view 26 (such as a center of the field of view) of the clinician 10 such that the clinician 10 may see his surroundings while viewing the magnified data stream of stereo images 22. However the magnified stream of stereo images 22 is preferably projected in a non-augmented manner at a fixed position and orientation in the field of view of the clinican 10.

In another example, the magnified data stream of stereo images 22 may fully occupy the field of view 26 of the clinician 10. Of course other similar configurations will be realized by a person of ordinary skill in the art in view of this specification.

The display devices 12, 15 may be connected to or form part of a computer system 100. The computer system 100 (also shown in FIG. 3) may include a tracking system 2 and a processor 122. The tracking system 2 may alternatively be separate from the computer system 100 and may form at least part of any of the devices, components, and/or systems discussed herein. The tracking system 2 can be optional and usable for variable augmented reality projections in which the patient and/or clinician 10 are tracked. Said tracking system may be electrically connected to a processor 122 and may offer real-time location data for a precise location and orientation of images and objects such as the data stream of stereo images 20 in a common coordinate system. In an exemplary embodiment herein, the tracking system may be sensor based e.g. based on a known position of the intra-oral camera 16 relative to surfaces of the intra-oral cavity being recorded.

The tracking system may also be vision based, for example as cameras for visual tracking of the patient 14, clinician 10, eyes of the clinician, features of the patient (such as the head or buccal cavity), and/or predetermined markers (not shown) placed on the patient 14. Said visual tracking may be achieved using, for example object/pattern recognition. A camera system 3 such as a 3D optical tracking system and/or stereoscopic camera system may be included in the computer system and/or may form or be a part of the tracking system 2. The intra-oral camera 16 may also form a part of or be the camera system 3. The camera system 3 may also be embedded in the display device 12 of the clinician 10. The camera system may operate under one of several depth sensing principles including, for example, (i) structural light, (ii) Time of Flight (ToF) and/or (iii) stereoscopic principles explained hereinafter. For cameras employing structural light, a light source may be used to project a known pattern onto the patient 14, and a receiver may detect the distortion of the reflected pattern to calculate depth map based on geometry. For cameras employing Time of Flight (ToF) principles, a light source may send out a pulse, and a sensor may detect a reflection of the pulse from the patient 14 in order to record it's time of flight. Knowing that and the constant speed of light, the system may calculate how far away the patient 14 is. Alternatively, light from a modulated light source may be sent and a phase change of light reflected from the patient may be detected. For cameras employing stereoscopic principles, multiple cameras may be placed at different positions to capture multiple images of the patient, and a depth map may be calculated based on geometry. This depth information may be used to track the patient's location during treatment (e.g. during dental treatment).

In yet another embodiment, the tracking system may be a fusion of sensor based and vision based tracking system. Moreover, any stereo camera mounted on the first display device 12 of the clinician may be used to acquire the data stream of stereo images 20 instead of the intra-oral camera 16, thereby freeing the clinician's upper limbs for other activities.

The processor 122 may be configured to receive the data stream of stereo images 20, to optionally analyze said data stream, to magnify the data stream of stereo images 20 according to one or more criteria (such as a magnification level) and to project the magnified data stream of stereo images 22 to a field of view of the clinician 10 in a fixed plane to form a stereoscopic video of the dental treatment site 14a, said stereoscopic video having a perception of depth. The processor 122 may further project other visualization information in an augmented manner to avoid overcrowding the field of view of the clinician due to overlapping projections. The magnified data may also be displayed virtually to the patient 14 through the second display device 15.

In an exemplary embodiment of the present invention, the magnified data stream of stereo images 22 and/or the visualization data may be projected in the field of view of the clinician 10 after a request is received from the clinician 10 through a user interface 126 of the computer system 100 (such as a gesture recognition system and/or a voice recognition system or the like).

Projection of the visualization data may be performed dynamically and in real time and may be achieved by the processor 122 working in tandem with the tracking system 2 wherein changes in position of (i) the patient 14 and/or (ii) the clinician 10, captured by the tracking system 2, may be translated into corresponding changes in positions of the overlaid data stream such that said data stream routed to a screen of the first display device 12 appears directly superimposed on target regions in a field of view 26 of the clinician 10 even as the patient 14 and/or or clinician 10 moves. In an exemplary embodiment of the present invention, the first display device 12 may be adapted to show patient information such as dental history and personal information as an augmentation in a field of view 26 of the clinician 10.

Computer System for Visualizing A Magnified Dental Treatment Site

Having described the visualization system 1 reference will now be made to FIG. 3, which shows a block diagram of a computer system 100 that may be employed in accordance with at least some of the example embodiments herein. Although various embodiments may be described herein in terms of this exemplary computer system 100, after reading this description, it may become apparent to a person skilled in the relevant art(s) how to implement the disclosure using other computer systems and/or architectures.

In one example embodiment herein, the computer system 100 may include at least one computer processor 122 and may include a tracking system 2, user interface 126 and input unit 130. The input unit 130 may be used by the clinician 10 along with a display unit 128 such as a monitor to send information to the computer processor 122. In one exemplary embodiment herein, the input unit 130 may be used to select a magnification level of the data stream of stereo images 20. In addition to showing the magnified data stream of stereo images 22 on the first display device 12 and the second display device 15, the magnified data stream of stereo images 22 may also be shown on a monitor. Herein one of the stereo channels may be routed to the monitor for display. In an embodiment, the input unit 130 may be a gesture/voice recognition device, a trackball, a mouse or other input device such as a keyboard or stylus. In one example, the display unit 128, the input unit 130, and the computer processor 122 may collectively form the user interface 126.

The computer processor 122 may include, for example, a central processing unit ("CPU"), a multiple processing unit, an application-specific integrated circuit ("ASIC"), a field programmable gate array ("FPGA"), or the like. The processor 122 may be connected to a communication infrastructure 124 (e.g., a communications bus, or a network). In an embodiment herein, the processor 122 may receive a request to display the magnified data stream of stereo images 22 and may obtain instructions concerning the request from one or more storage units of the computer system 100. The processor 122 may then load said instructions and execute the loaded instructions.

Figure 4:
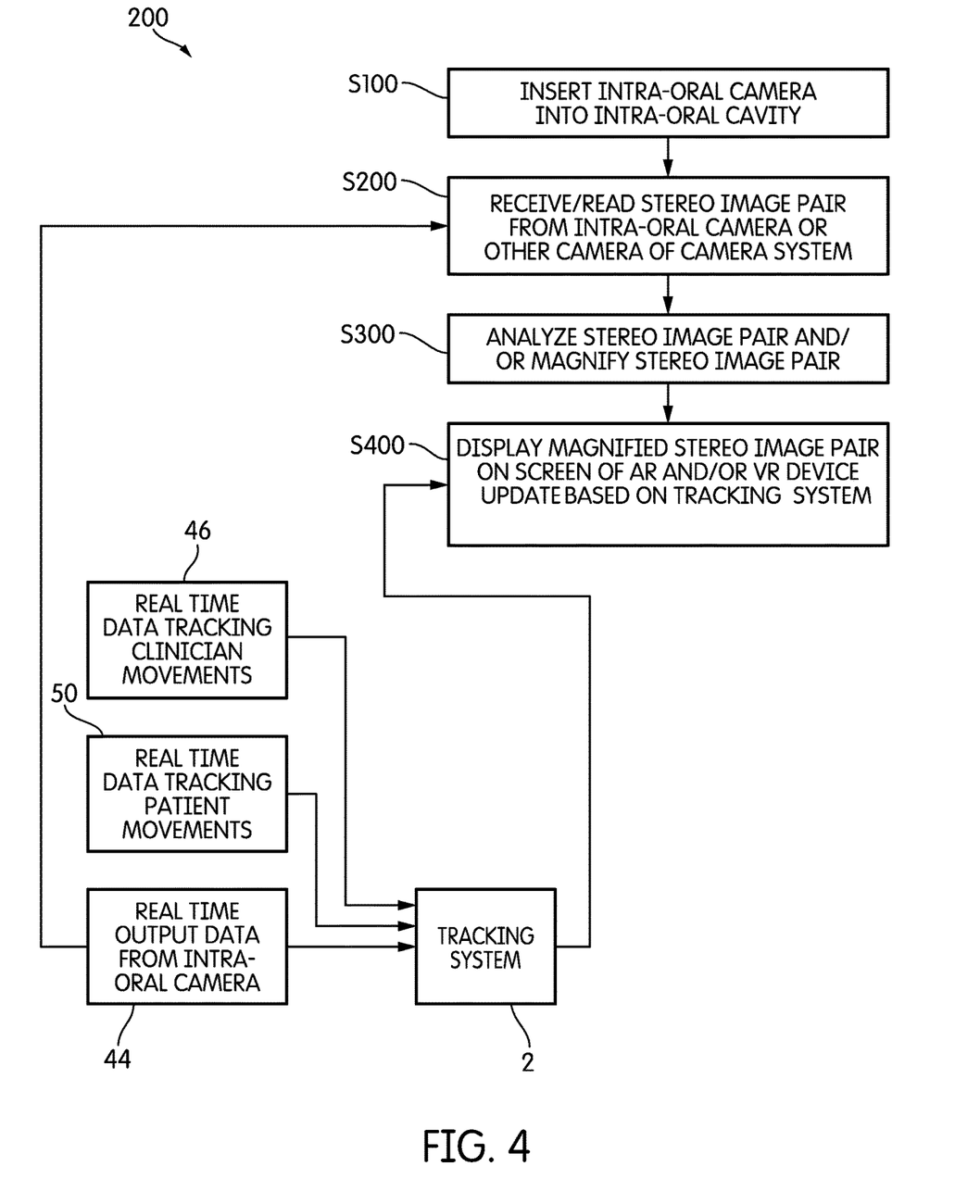
FIG. 4 is a flow chart showing a method according to an embodiment of the present invention.

One or more steps/procedures for visualizing the magnified data stream of stereo images may be stored on a non-transitory storage device in the form of computer-readable program instructions. To execute a procedure, the processor 122 loads the appropriate instructions, as stored on a storage device, into memory and then executes the loaded instructions as shown in FIG. 4 discussed hereinafter.

The computer system 100 may further comprise a main memory 132, which may be a random-access memory ("RAM") and may include a secondary memory 134. The secondary memory 134 may include, for example, a hard disk drive 136 and/or a removable-storage drive 138 (e.g., a floppy disk drive, a magnetic tape drive, an optical disk drive, a flash memory drive, and the like). The removable-storage drive 138 may read from and/or write to a removable storage unit 140 in a well-known manner. The removable storage unit 140 may be, for example, a floppy disk, a magnetic tape, an optical disk, a flash memory device, and the like, which may be written to and read from by the removable-storage drive 138. The removable storage unit 140 may include a non-transitory computer-readable storage medium storing computer-executable software instructions and/or data.

In further alternative embodiments, the secondary memory 134 may include other computer-readable media storing computer-executable programs or other instructions to be loaded into the computer system 100. Such devices may include a removable storage unit 144 and an interface 142 (e.g., a program cartridge and a cartridge interface); a removable memory chip (e.g., an erasable programmable read-only memory ("EPROM") or a programmable read-only memory ("PROM")) and an associated memory socket; and other removable storage units 144 and interfaces 142 that allow software and data to be transferred from the removable storage unit 144 to other parts of the computer system 100.

The computer system 100 also may include a communications interface 146 that enables software and data to be transferred between the computer system 100 and external devices. Such an interface may include a modem, a network interface (e.g., an Ethernet card or an IEEE 802.11 wireless LAN interface), a communications port (e.g., a Universal Serial Bus ("USB") port or a FireWire® port), a Personal Computer Memory Card International Association ("PCM-CIA") interface, Bluetooth®, and the like. Software and data transferred via the communications interface 146 may be in the form of signals, which may be electronic, electromagnetic, optical or another type of signal that may be capable of being transmitted and/or received by the communications interface 146. Signals may be provided to the communications interface 146 via a communications path 148 (e.g., a channel). The communications path 148 may carry signals and may be implemented using wire or cable, fiber optics, a telephone line, a cellular link, a radio-frequency ("RF") link, or the like. The communications interface 146 may be used to transfer software or data or other information between the computer system 100 and a remote server or cloud-based storage (not shown).

One or more computer programs or computer control logic may be stored in the main memory 132 and/or the secondary memory 134. The computer programs may also be received via the communications interface 146. The computer programs may include computer-executable instructions which, when executed by the computer processor 122, cause the computer system 100 to perform the methods as described hereinafter.

In another embodiment, the software may be stored in a non-transitory computer-readable storage medium and loaded into the main memory 132 and/or the secondary memory 134 of the computer system 100 using the removable-storage drive 138, the hard disk drive 136, and/or the communications interface 146. Control logic (software), when executed by the processor 122, causes the computer system 100, and more generally the system 1, to perform all or some of the methods described herein.

Implementation of other hardware arrangement so as to perform the functions described herein will be apparent to persons skilled in the relevant art(s) in view of this description.

Method for Visualizing A Magnified Treatment Site.

Figure 3:
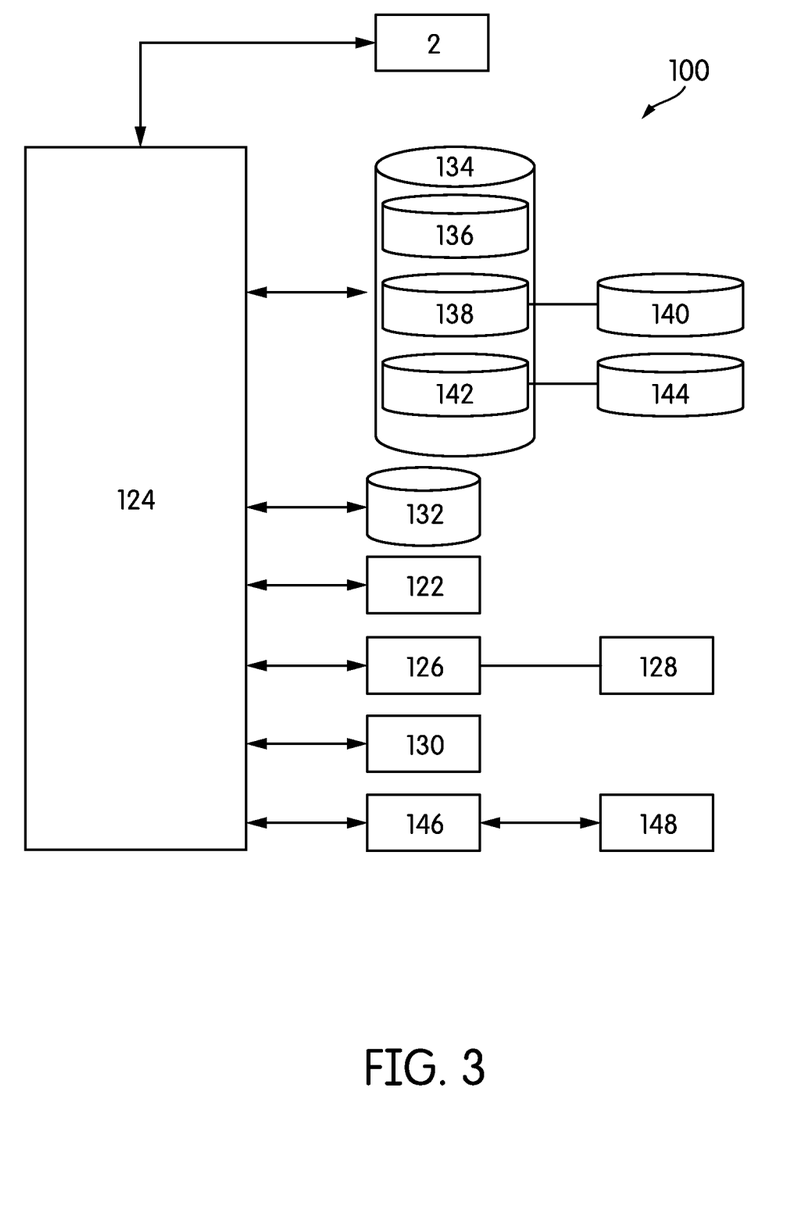
FIG. 3 illustrates a block diagram of a computer system of the present invention.

Having described the computer system 100 of FIG. 3, methods for visualizing a magnified treatment site will now be further described in conjunction with FIG. 4.

FIG. 4 shows a process 200 for visualizing a magnified dental treatment site. The process may start when a clinician 10 inserts an intra-oral camera 16 into an oral cavity (Step S100). Raw Data from the intra-oral camera 16 may then be received/read (Step S200). This raw data may then be analyzed, modified (such as changing its color space or brightness to highlight certain colors or enhance the image contrast) and/or magnified (Step S300) according to a defined magnification level in order to show a magnified treatment site for the clinician 10 and the patient 14. The modification can involve shifting the tooth color, for example in the yellow/red direction (or in the opposite direction) to increase or reduce the visible impression of discoloration or plaque. Moreover, the intra-oral camera 16 may provide a illumination of the treatment site 14a such that the display devices (VR glasses and/or augmented reality glasses) may automatically generate an enlarged, well-lit and spatially displayed (three-dimensional) view in real time.

This enlarged three-dimensional view/magnified data stream of stereo images 22 is thus projected using the first display unit 12 and/or second display device 15 (Step S400). Further, the orientation of the displayed images (eg . . . The visualization information) may be updated in real time based on the tracking system 2. For example, using data from the tracking system 2 including, (i) real time data tracking clinician movements 46 (ii) real time data tracking patient movements 50, and/or (iii) real time output data from the intra-oral camera 44, the orientation and/or location of the magnified data stream of stereo images 22 routed to the first display device 12 may be dynamically updated in real time for overlay on the treatment site 14a or otherwise any other predetermined real world site in a field of view 26 of the clinician 10 such that said augmentation appears directly superimposed on said site. In an exemplary embodiment of the present invention, the visualization information is displayed in an empty space in the field of view of the clinician that does not include the patient's oral cavity. Said empty space may be recognized using, for example, object recognition on data obtained from the camera system 3 or intraoral camera 12. Moreover, the orientation and/or location of the magnified data stream of stereo images 22 routed to second display device 15 may be dynamically updated in real time for virtual display to the patient 14 such that the patient may see the same view of the magnified data stream of stereo images 22 seen by the clinician 10.

In an embodiment of the present invention, the magnified data stream of stereo images 22 may be displayed simultaneously on several 3D display devices. In a further embodiment, the intra-oral camera 16 is connected to a PC (Personal computer) or laptop via an existing GigE connection. Stereo image pairs generated by the intra-oral camera 16 may be read out by an application in the PC and sent in real time via a wireless connection to a pair of AR and/or VR glasses. Herein, the left stereo channel of the glasses may be displayed on the left eye of the viewer and the right stereo channel of the glasses may be displayed for the right eye. At the same time, the image may be viewed via a patient monitor which may also be connected to the PC. The clinician 10 may guide the intra-oral camera 16 through the patient's mouth. While the dentist dictates tooth by tooth to an assistant his/her respective findings, the patient receives a spatially displayed, enlarged representation of the respective area/tooth.

In view of the foregoing description, it may be appreciated that the example embodiments described herein provide a method, system and computer readable storage media for visualizing a magnified dental treatment site.

Unless otherwise defined, all technical and scientific terms used herein have the same meaning as commonly understood by one of ordinary skill in the art to which this invention belongs. Although methods and materials similar to or equivalent to those described herein may be used in the practice or testing of the disclosure, suitable methods and materials are described above. All publications, patent applications, patents, and other references mentioned herein are incorporated by reference in their entirety to the extent allowed by applicable law and regulations. The disclosure may be embodied in other specific forms without departing from the spirit or essential attributes thereof, and it may therefore be desired that the present embodiment be considered in all respects as illustrative and not restrictive. Any headings utilized within the description are for convenience only and have no legal or limiting effect.

What is claimed is:

1. A method for visualizing a magnified dental treatment site, the method comprising the steps of:
    obtaining a data stream of stereo images from an intra-oral camera, the data stream of stereo images being a live data stream of stereo image pairs that are offset and show a dental treatment site from different perspectives;
    magnifying said data stream of stereo images, and
    projecting, in a first display device in a field of view of a user of the first display device and at a fixed distance and orientation relative to said field of view, a right and a left portion of the magnified data stream of stereo images to create a combined view of the dental treatment site having a perception of 3D depth,
    wherein the projected right and left portion of the magnified data stream of stereo images is viewed by a shift of eye focus to thereto.

2. The method according to claim 1, wherein visualization information is projected at variable distances and orientations relative to the field of view of the user.

3. The method according to claim 2, wherein the visualization information includes at least one of a magnification level, a resolution and a working distance.

4. The method according to claim 1, wherein the data stream of stereo images is magnified according to a predetermined magnification level.

5. The method according to claim 1, further comprising the step of changing the mage content by using color space transformations or enhancing the contrast of the data stream of stereo images for diagnostic purposes.

6. The method according to claim 1, wherein said data stream of stereo images is obtained in real-time.

7. The method according to claim 2, further comprising the step of overlaying the visualization information as an augmentation on a predetermined site in the field of view such that said visualization information appears directly superimposed on said predetermined site.

8. The method according to claim 1, further comprising the step of projecting said magnified data stream of stereo images as virtual objects using a second display device adapted for virtual reality.

9. The method according to claim 1, further comprising the step of displaying the magnified data stream from one stereo channel of the intra-oral camera on a monitor.

10. The method according to claim 7 further comprising the step of; updating the augmentation based on data being selected from the group consisting of (i) real time output data from the intra-oral camera (ii) real time data tracking clinician movements and (iii) real time data tracking patient movements.

11. A system for visualizing a magnified dental treatment site, the system comprising:
    at least one processor configured to perform the steps of;
        obtaining a data stream, of stereo images from an intra-oral camera, the data stream of stereo rages being a live data stream of stereo image pairs that are offset and show a dental treatment site from different perspectives;
        magnifying said data shearer of stereo images; and
        projecting, in a first display device in a field of view of a user of the first display device and at a fixed distance and orientation relative to said field of view, a right and a left portion of the magnified data stream of stereo images to create a combined view of the dental treatment site having a perception of 3D depth
    wherein the projected right and left portion of the magnified data stream of stereo images is viewed by a shift of eye focus to thereto.

12. The system according to claim 11, wherein visualization information is projected at variable distances and orientations relative to the field of view of the user.

13. The system according to claim 11, wherein the data stream of stereo images is magnified according to a predetermined magnification level.

14. The system according to claim 11, further comprising the step of changing the image content by using color space transformations or enhancing the contrast of the data stream of stereo images for diagnostic purposes.

15. The system according to claim 11, wherein said data stream of stereo images is obtained in real-time.

16. A non-transitory computer-readable storage medium storing a program which, when executed by a computer system causes the computer system to perform a procedure comprising the steps of:
  obtaining a data stream of stereo images from an intra-oral camera, the data stream of stereo images being a live data stream of stereo image pairs that are offset and show a dental treatment site from different perspectives;
  magnifying said data stream of stereo images; and
  projecting, in a first display device in a field of view of a user of the first display device and at a fixed distance and orientation relative to said field of view a right and a left portion of the magnified data stream of stereo images to create a combined view of the dental treatment site having a perception of 3D depth
  wherein the projected right and left portion of the magnified data stream of stereo images is viewed by a shift of eye focus to thereto.

* * * * *